(12) United States Patent
Dhuper et al.

(10) Patent No.: US 7,861,713 B2
(45) Date of Patent: Jan. 4, 2011

(54) ADAPTER FOR USE IN AN AEROSOL DELIVERY SYSTEM

(76) Inventors: Sunil Kumar Dhuper, 47 Red Ground Rd., Old Westbury, NY (US) 11568; Herbert Fred D'Alo, 37 Forest Hills Dr., Madison, CT (US) 06443

( * ) Notice: Subject to any disclaimer, the term of this patent is extended or adjusted under 35 U.S.C. 154(b) by 850 days.

(21) Appl. No.: 11/450,974

(22) Filed: Jun. 8, 2006

(65) Prior Publication Data

US 2007/0283954 A1 Dec. 13, 2007

(51) Int. Cl.
*A61M 15/08* (2006.01)
(52) U.S. Cl. .................. 128/203.24; 128/200.23; 128/200.14; 128/203.12; 128/203.15; 128/203.29; 128/203.11; 128/202.28; 128/202.29; 128/207.12; 128/207.16; 128/205.24
(58) Field of Classification Search ............ 128/200.23, 128/200.14, 203.12, 203.15, 203.29, 203.11, 128/202.28, 202.29, 207.12, 207.16, 205.24
See application file for complete search history.

(56) References Cited

U.S. PATENT DOCUMENTS

| | | | |
|---|---|---|---|
| 4,210,155 A | 7/1980 | Grimes | |
| 4,470,412 A | 9/1984 | Nowacki et al. | |
| 4,637,528 A | 1/1987 | Wachinski et al. | |
| 4,641,644 A | 2/1987 | Andersson et al. | |
| 4,953,545 A | 9/1990 | McCarty | |
| 5,012,803 A | 5/1991 | Foley et al. | |
| 5,385,140 A | 1/1995 | Smith | |
| 5,752,502 A | 5/1998 | King | |
| 5,816,240 A * | 10/1998 | Komesaroff | 128/200.23 |
| 6,705,316 B2 * | 3/2004 | Blythe et al. | 128/204.18 |
| 2002/0069870 A1 * | 6/2002 | Farmer | 128/200.22 |
| 2002/0121275 A1 | 9/2002 | Johnson | |
| 2002/0129814 A1 | 9/2002 | Sladek | |

FOREIGN PATENT DOCUMENTS

WO WO-2005/010274 10/2005

OTHER PUBLICATIONS

International Search Report and Written Opinion of the International Searching Authority for PCT/US07/70232 dated Aug. 27, 2008.

* cited by examiner

*Primary Examiner*—Patricia M Bianco
*Assistant Examiner*—Nihir Patel
(74) *Attorney, Agent, or Firm*—Leason Ellis LLP (57) ABSTRACT

According to one aspect of the present invention, an aerosol inhalation system includes a first conduit member for delivering medication in the form of aerosol particles to a patient. The system also includes a first device in fluid communication with the first holding chamber for producing the aerosol particles and being sealingly yet releasably received within an adapter that forms an entrance into a first holding chamber. The adapter has a compressible material disposed thereon which is at least partially compressed by insertion of the first device to form the seal between the first device and the adapter, thereby creating a closed system that is therefore capable of delivering a fixed concentration of the medication to the patient due to a valve of the valve mechanism being closed when the patient inhales and the medication is delivered to the patient.

23 Claims, 4 Drawing Sheets

ADAPTER FOR USE IN AN AEROSOL DELIVERY SYSTEM

TECHNICAL FIELD

The present invention relates to inhalation equipment and more particularly, relates to aerosol inhalation systems including an interface (interface element) for use in the system between a conventional part of the inhalation equipment, such as a generator, and the patient, with an adapter being provided as a part thereof for mating with an aerosol delivery device, such as a metered dose inhaler (MDI).

BACKGROUND

Aerosol inhalation equipment is commonly used as a means to deliver medication in an aerosolized form to a patient. Aerosolized medication is typically used to treat patients with respiratory conditions, such as asthma or chronic obstructive pulmonary disease (COPD). For example, inhalation equipment is a common means for delivering medication to counter certain aliments of a patient population, including reactive airway disease, asthma, cystic fibrosis, etc.

It is generally accepted that effective administration of medication as aerosol depends on the delivery system and its position in relation to the patient. Aerosol particle deposition is influenced by particle size, ventilatory pattern, and airway architecture and effective medication response is also influenced by the dose of the medication used.

An aerosol delivery system includes three principal elements, namely a generator, a power source, and an interface. Generators include small volume nebulizers (SVN), large volume nebulizers (LVN), metered dose inhalers (MDI), and dry powder inhalers (DPI). The power source is the mechanism by which the generator operates or is actuated and includes compressed gas for SVN and LVN and self-contained propellants for MDI. The interface is the conduit between the generator and the patient and includes spacer devices/accessory devices with mouthpieces or face masks. Depending on the patient's age (ability) and coordination, various interfaces are used in conjunction with SVN and MDI in order to optimize drug delivery.

A SVN is a jet nebulizer that is powered by a compressed gas source. The medication is displaced up a capillary tube from the nebulizer's reservoir and is dispersed continuously as aerosolized particles. The aerosolized particles are spontaneously inhaled by the patient or delivered in conjunction with positive-pressure breaths. Typically, for patients greater than 3 years who are spontaneously breathing without an artificial airway and are able to cooperate, a mouthpiece with an extension reservoir should be used. For patients unable to negotiate a mouthpiece, typically children under 3 years, a face mask should be used.

An MDI is essentially a pressurized canister that contains a medication and propellant. Actuation of the MDI results in the ejection of one dose of medication as aerosolized particles, which can be spontaneously inhaled by the patient or delivered in conjunction with positive-pressure breaths. A spacer device/accessory device should be used with an MDI. A spacer device enhances delivery by decreasing the velocity of the particles and reducing the number of large particles. A spacer device with a one-way valve, i.e., holding chamber, eliminates the need for the patient to coordinate actuation and inhalation and optimizes drug delivery. A spacer device without valves requires coordination between inhalation and actuation. The MDI with spacer device and face mask is appropriate for patients, typically less than 3 years, unable to use a mouthpiece.

A DPI is a breath-actuated device that uses a gelatin capsule containing a single dose of medication and a carrier substance to aid in the dispersion of the drug. The capsule is inserted into the device and punctured. The patient's inspiratory flow disperses the dry particles and draws them into the lower airways. In spontaneously breathing patients, this device is appropriate in patients who are able to achieve a certain inspiratory flow, such as equal to or greater than 50 L/min. This will typically correspond to children about 6 years or greater.

A LVN can be used to deliver a dose of medication continuously over a period of time. A LVN is powered by a compressed gas source, and a face mask is typically used as the interface.

The two primary means for delivering aerosolized medication to treat a medical condition is an MDI or a nebulizer. MDI medication (drug) canisters are typically sold by manufacturers with a boot that includes a nozzle, an actuator, and a mouthpiece. Patients can self-administer the MDI medication using the boot alone but the majority of patients have difficulty in synchronizing the actuation of the MDI canister and patient inhalation and improve the delivery of medication by decreasing oropharyngeal deposition of the aerosol drug.

Many valved chambers of this type are commercially available. Examples of such spacers include but are not limited to those structures disclosed in U.S. Pat. Nos. 4,470,412; 5,012,803; 5,385,140; 4,637,528; 4,641,644; 4,953,545; and U.S. patent application publication Ser. No. 2002/0129814. These devices are expensive and may be suitable for chronic conditions that require frequent use of MDI inhalers provided the cost and labor involved in frequent delivery of medication is acceptable to the patient. However, under acute symptoms, such devices may fail to serve the purpose and lead to an inadequate delivery of medication.

Aerosol delivery systems that use standard small volume nebulizers are commonly used in acute conditions as they are cheap and overcome the inhalation difficulties associated with actuation of MDI and synchronization of inhalation by the patient. Nebulizers are fraught with numerous problems as well. The medication does used is about 10 times of that used with an MDI and hence the increased cost without any added proven clinical benefit. Secondly, the majority of the nebulized medication is wasted during exhalation. Thirdly, the time taken to deliver the medication is several times that of an MDI and the labor cost of respiratory therapist may outweigh the benefits of nebulizers compared with MDIs. Breath actuated nebulizers(s) with reservoir have been designed to overcome the medication waste. An example of this type of device is found in U.S. Pat. No. 5,752,502. However, these devices are expensive and still have all the other problems associated with nebulizer use alone. In addition, the time taken to deliver the medication with the breath actuated device may vary from three to six times (depending on the ratio of inspiratory to expiratory time) greater than the time taken with the conventional nebulizer to deliver the same dose of medication. Other examples of aerosol inhalation devices can be found in U.S. Pat. No. 4,210,155, in which there is a fixed volume mist accumulation chamber for use in combination with a nebulizer and a TEE connection.

Problems with prior art devices include that the devices significantly waste medication, they provide a non-uniform concentration of delivered medication, they provide a non-uniform concentration of delivered gas, they are expensive, and they are difficult to use. Many of these devices are commercially available in which the nebulizer is directly attached to the TEE connector without any mixing chamber. All of the aforementioned devices can be used with either an MDI or a nebulizer but not both, and hence, face the difficulty associated with either system alone. Other devices have tried to overcome the above problems by incorporating a mixing chamber in the device with adaptability to be used with an MDI or standard nebulizer. U.S. patent application publication Ser. No. 2002/0121275 disclosed a device having the above characteristics. However, this device is plagued with problems that are typical to those type of devices. As with other conventional devices, the disclosed device, like the other ones, fails to incorporate some of the key features necessary for enhanced aerosol delivery.

In general, each of the prior art devices suffers from the following deficiencies: (1) the entrained airflow in the device interferes with the MDI plume as well as the plume generated by a nebulizer resulting in increased impaction losses of aerosol generated by either an MDI or nebulizer; (2) the device does not have the ability to deliver a desired precise fraction of inspired oxygen to a hypoxic patient and simultaneously deliver aerosol medication with either a metered dose inhaler (MDI) or a nebulizer; (3) the device can not deliver a gas with a desired density to improve aerosol delivery and a desired fraction of inspired oxygen to a hypoxemic patient; (4) the device does not have the ability to deliver different density gases with a desired fraction of inspired oxygen simultaneously while retaining the ability to deliver aerosol medication at the same time with either an MDI or a nebulizer; (5) the device does not have the ability to deliver a mixture of multiple gases to a patient and simultaneously maintain a desired fraction of inspired oxygen; (6) the device does not serve as a facemask for delivering varying concentrations of inspired oxygen from room air to 100% but serves solely as an aerosol delivery device; (7) the device does not have a reservoir chamber—either as a bag or as a large volume tubing to store nebulized medication that is otherwise wasted during exhalation (The holding chamber of this type of device varies from 90 cc to 140 cc and is not enough to serve as a reservoir for the volume of nebulized medication generated during exhalation which is, therefore, wasted); (8) there is no mechanism in the device to prevent entrainment of room air which forms the bulk of volume during inhalation (the fraction of inspired oxygen and the density of the gas mixture inhaled by the patient may vary with every breath with the device depending on the volume of entrained room air which may vary with each breath); (9) the device does not have any valve system to prevent exhaled carbon dioxide from entering the holding chamber—rebreathing of carbon dioxide from the holding chamber on subsequent inhalation can be extremely detrimental to a patient and extremely dangerous under certain clinical conditions; (10) the device does not have the capability of delivering medication with an MDI and a nebulizer simultaneously; and (11) the device has a fixed volume-holding chamber, which makes the device extremely large and cumbersome to deliver medication.

What is needed in the art and has heretofore not been available is a system that overcomes the above deficiencies and incorporates functionality to make the device a compact, user friendly, economical, and multipurpose aerosol device for both acute and chronic use with either an MDI or a nebulizer or with both devices simultaneously as warranted by the patient's clinical circumstances.

SUMMARY

According to one aspect of the present invention, an aerosol inhalation system includes a first conduit member for delivering medication in the form of aerosol particles to a patient. The system includes a first holding chamber for holding the aerosol particles prior to deliver to the first conduit member and a valve mechanism associated with the first conduit member and includes a first valve assembly and a second valve assembly. The first valve assembly is positionable between an open position and a closed position where the fluid is prevented from flowing between the first holding chamber and the first conduit member as when the patient exhales. In particular, the first valve assembly assumes the open position as the patient inhales and the second valve assembly is positionable between an open position where the first conduit member is vented to atmosphere as when the patient exhales and a closed position when the patient inhales and the first valve assembly opens.

The system also includes a first device in fluid communication with the first holding chamber for producing the aerosol particles and being sealingly yet releasably received within an adapter that forms an entrance into the first holding chamber. The adapter has a compressible material disposed thereon which is at least partially compressed by insertion of the first device to form the seal between the first device and the adapter. The aerosol inhalation apparatus is a closed system and is therefore capable of delivering a fixed concentration of the medication to the patient due to the second valve assembly being closed when the patient inhales and the medication is delivered to the patient.

In one embodiment, the device is in the form of a metered dose inhaler (MDI).

In one exemplary embodiment, the compressible material is a foam material or a highly compressible rubber. The compressible material can be provided not only on an inner surface of the adapter but can also be provided on an outer surface as well, in which case, the compressible material extends from the inner surface across the upper edge of the adapter to the outer surface.

When the device (MDI) is not in use, a plug or cap can be placed into the adapter for sealing thereof. The plug or cap is frictionally fit to an open end of the adapter. The cap or plug has a plurality of vent openings formed therethrough. A valve member is provided and is operatively coupled to the plug or cap and is in selective communication with the vent openings such that in a closed position, the valve member prevents air to the vent openings and in an open position, the valve member permits air to flow through the vent openings into the holding chamber. The valve member can be a flexible membrane that is attached to an underside of the cap in a central region between the vent openings with outer peripheral edges of the flexible membrane covering the vent openings in the closed position.

Further aspects and features of the exemplary aerosol inhalation system disclosed herein can be appreciated from the appended Figures and accompanying written description.

BRIEF DESCRIPTION OF THE DRAWING FIGURES

The foregoing and other features of the present invention will be more readily apparent from the following detailed description and drawings of the illustrative embodiments of the invention wherein like reference numbers refer to similar elements and in which.

DETAILED DESCRIPTION OF PREFERRED EMBODIMENTS

Figure 1:
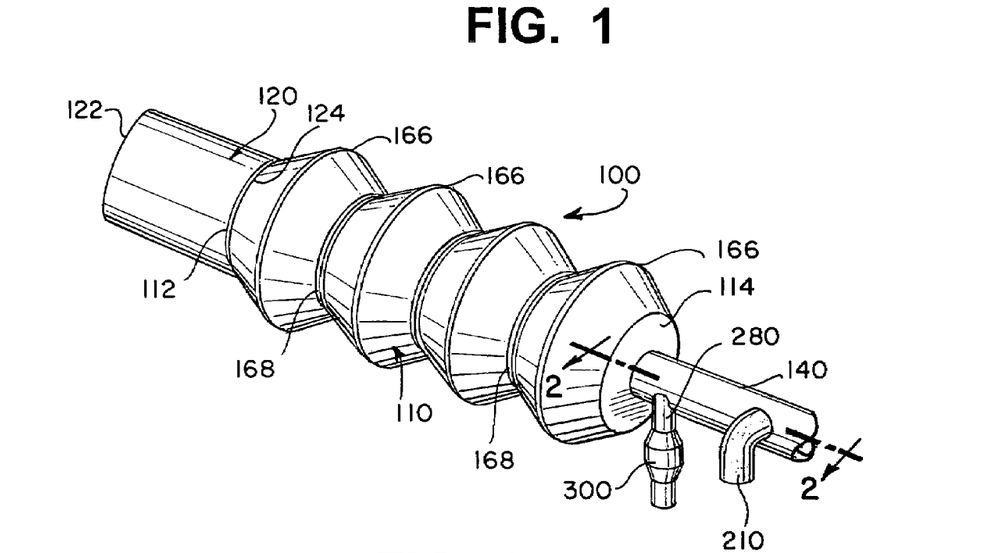
FIG. 1 is a perspective view of an aerosol inhalation system.
Figure 2:
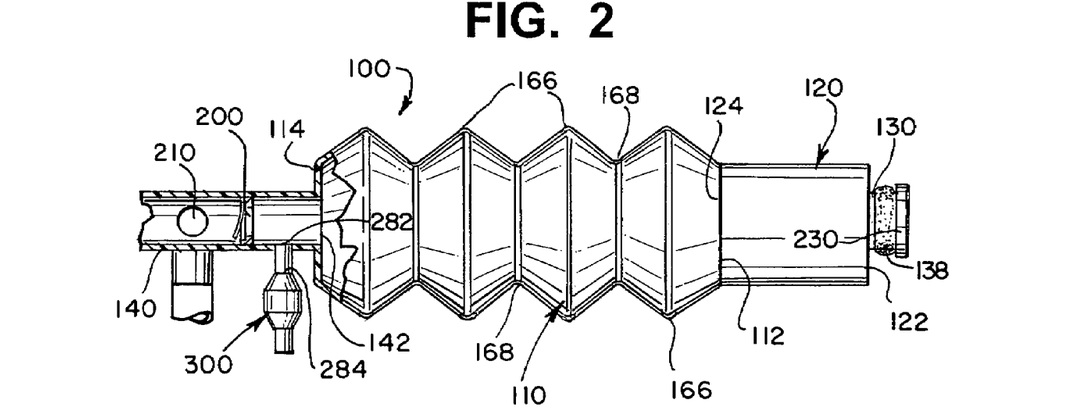
FIG. 2 is a side elevation view, in partial cross-section, of the system of FIG. 1 with an adapter according to a first embodiment with a seal member disposed on inner and outer surfaces of the adapter, with a cap fitted thereto.
Figure 2A:
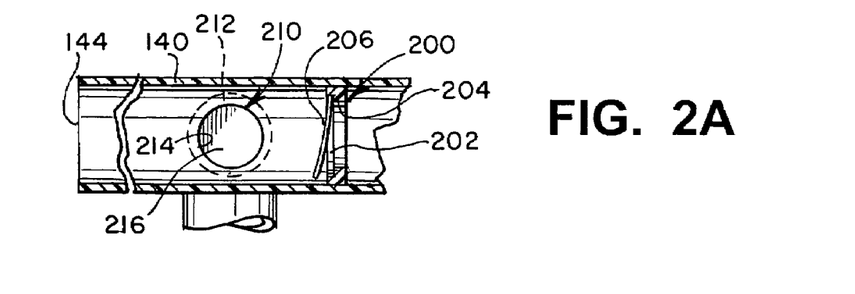
FIG. 2A is an enlarged partial cross-sectional view of a valve mechanism within the system of FIG. 1.

Now turning to FIGS. 1-2A in which an aerosol delivery system 100 according to one embodiment is illustrated. The system 100 is constructed and adapted for use with a metered dose inhaler (MDI) or a nebulizer or both.

As previously mentioned, one of the disadvantages of prior nebulizer systems is that the nebulizer is not able to deliver a fixed concentration of medication to the patient since the nebulizer system includes a vented outlet conduit or tube that connects to a mask or the like to permit the suspended medication to be delivered into the patient's body. More particularly, this outlet conduit simply contains a vent opening or the like which permits atmospheric air to flow into the outlet conduit and mix with the nebulized medication that is delivered into the outlet conduit from a holding chamber or the like. It will be appreciated that this results in a mixing of the medication with atmospheric air and this results in the concentration of the medication being diluted due to the presence of air. This is not desirable since it results in medication being delivered at less than a desired concentration as a result of the dilution of the medication by the air.

According to one embodiment, the system 100 includes two defined chambers or compartments, namely a first chamber (holding chamber) 110 and a second chamber (holding chamber) 120 when the system 100 is constructed to function as an MDI delivering device and a nebulizer accessory. The first chamber 110 has an inlet end 112 as well as an opposing outlet end 114 and similarly, the nebulizer chamber 120 has an inlet end 122 and an opposing outlet end 124.

The first chamber 110 is also operatively coupled to an outlet conduit member 140 that is disposed at the outlet end 114 of the first chamber 110. Similar to the other conduit members, the outlet conduit member 140 has an inlet end 142 and an opposite outlet end 144, with the inlet end 142 being in fluid communication with the interior of the first chamber 110.

According to the present invention, the first chamber 110 is preferably a holding chamber that has an adjustable interior volume and therefore, the volume of the first chamber 110 can be advantageously varied depending upon a number of different parameters, such as the type of patient and more specifically, the weight of the patient. There is a direct correlation between the weight of the patient, and lung capacity, and the volume of the holding chamber 110 in that the greater the weight of the patient, the greater the required volume of the holding chamber 110. In accordance with one aspect of the invention, the volume of the first chamber 110 can be chosen between a number of different selected volumes so as to cater and customize the system 100 for the specific patient. The different settings can be marked on the first chamber 110 or they can be otherwise conveyed to the physician who then merely manipulates the body forming the first chamber 110 so that the volume of the first chamber 110 is within the desired range.

For example, the settings corresponding to the volume of the first chamber 110 can be (1) infant; (2) young child; (3) pre-teen child; (4) teenager; (5) young adult; (6) adult; and (7) elderly. Similarly, the settings corresponding to the volume of the first chamber 110 can be directly correlated to a mass size, such as (1) less than 20 pounds; (2) less than 60 pounds; (3) less than 100 pounds; (4) less than 150 pounds; (5) less than 200 pounds, etc. After determining what the proper setting should be, the physician can then manipulate the first chamber structure to cause the volume within the first chamber 110 to be set at the desired value. In each of the embodiments, the structure defining the first chamber 110 can be manually manipulated resulting in the interior volume of the first holding chamber either being increased or decreased. For example and according to one embodiment, the first chamber 110 can be formed by a first part and a second part that is at least partially received in the interior of the first part and slidingly engages the first part such that when it is desired for the interior volume of the first chamber 110 to be changed, the user simple moves the second part relative to the first part resulting in the interior volume either increasing or decreasing. Accordingly, a pair of slide single open-ended tubular structures can be mated together such that they can slide with respect to one another. The structures can contain markings, settings, or graduations so that it is easy for the user to simple adjust one of the parts with respect to the other part until it is in registration with some type of guide line that represents or indicates the volume of the interior of the first chamber 110. In order to provide a sealed first chamber 110, the first and second parts preferably contain some type of seal element that ensures an air-tight seal therebetween. For example, one or both of the first and second parts can contain an O-ring or the like that sealingly engages a surface of the other part while still permitting sliding movement between the two parts.

It will be appreciated that the first and second parts can also be fitted with a locking type mechanism so as to permit the position of the first part relative to the second part to be locked in place. For example, the first part can be at least partially received in the second part such that the first part at least partially surrounds the second part, with the first part having a number of axially aligned opening formed therein. Each opening corresponds to a different interior volume setting. The second part can include a biased projection that protrudes out from the exterior surface thereof and in one particular embodiment, the biased projection is a spring biased push button that can be depressed upon application of force and will return to its original biased position when the applied force is removed. When the second part is received in the first part, the biased projection is in a biased condition and is at least partially depressed and exerting a force against an inner surface of the first part until the projection comes into registration with one of the openings at which time, the biased nature of the projection causes the projection to fire into the opening, thereby locking the position of the first part relative to the second part. To freely adjust the interior volume of the first chamber 110, the projection can simply be depressed until it clears the first part and then the second part can be moved relative to the first part in a direction toward the next desired opening at which time the projection is received in the opening, thereby locking the two parts in a different setting with a different interior volume.

The first chamber 110 can be made of any number of different materials, including plastic, paper or even a metal so long as the interior volume thereof can be varied. According to one embodiment, the first chamber 110 can have a cylindrical shape with smooth edges or it can by cylindrical in shape with a series of ridges 166 and recesses or valleys 168 that alternate with one another so as to represent a bellows or accordion type structure. Alternatively, the first chamber 110 can be supported with a metal or plastic coil that includes multiple ring structures so as to support the material that defines the body of the first chamber 110. The distances between any two adjacent ridges 166 can be equal as in the case of a uniform structure or the distances can be different. In another embodiment, the first chamber 110 can be formed of a stiff corrugated plastic that preferably does not require any additional support to maintain the shape of the first chamber 110. FIG. 1 shows the first chamber 110 in an expanded state (e.g., fully expanded state), while FIG. 2 shows the first chamber 110 in a fully collapsed state. It will be appreciated that the first chamber 110 can be constructed in any number of different ways so long as the first chamber 110 has a variable interior volume.

The second chamber 120 is similar to the first chamber 110 and includes an inlet end 122 and an opposite outlet end 124 and can be formed to have any number of different shapes. For example and as illustrated, the second chamber 120 is a generally hollow holding member that has a cylindrical shape; however, the second chamber 120 can be formed in other shapes, including regular shapes, such as rectangular, and irregular shapes, and can even have the shape of the first chamber 110. In other words, the second chamber 120 can have a fixed volume or it can have a variable volume, similar to the expandable/retractable first chamber 110 (e.g., bellows structure).

In the illustrated embodiment, the inlet end 112 of the first chamber 110 and the outlet end 124 of the second chamber 120 are securely coupled to one another. For example, the ends 112, 124 can be bonded or fused to one another along an interface edge therebetween which in this case is a circumferential edge since both chambers 110, 120 are cylindrical in shape. Any number of means for bonding or otherwise securely attaching these two ends 112, 124 to one another can be used. For example, the two can be heat sealed or adhesively bonded to one another or fused to one another. In this figure, the first chamber 110 is shown in the fully expanded state.

As described in great detail below, the second chamber 120 has an adapter, boot, or connector 130, according to the present invention, formed at the inlet end 122 thereof to permit a secure and preferably, sealed, connection with a medication delivery device 170 (FIG. 3), which in the illustrated embodiment is an inhaler (MDI), that can removed when not in use. Thus, upon actuation of the inhaler 170, the aerosol particles generated by the MDI 170 are discharged into the second chamber 120 and then into the first chamber 110.

Figure 3:
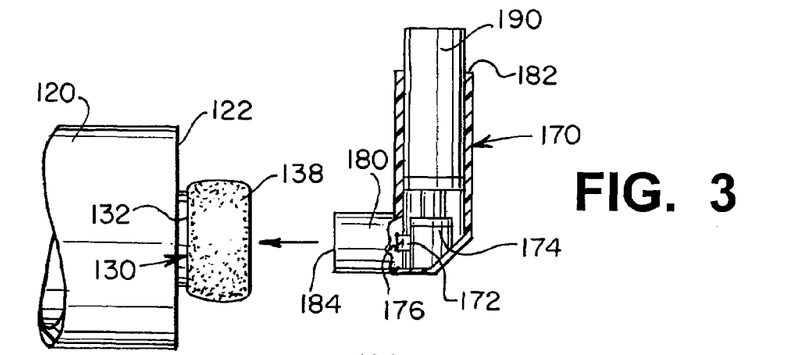
FIG. 3 is an enlarged side elevation view of the adapter of FIG. 2 with a medication delivery device being exploded therefrom and shown in cross-section.

The MDI 170 can be any number of commercially available inhalers that are configured to deliver a metered dose of medication, etc. Typically, the MDI 170 has a boot structure 180 that has an inlet end 182 and an opposing outlet end 184. The illustrated boot structure 180 is generally an L-shaped hollow structure with the outlet end 184 being formed in a boot section that is perpendicular to another section that terminates with the inlet end 182. A canister 190 is introduced into the boot structure 180 through the inlet end 182 of the boot 180 and a nozzle 172 of the inhaler 170 is attached to an actuator 174. The actuator 174 has an opening or slot 176 formed therein and preferably, the actuator 174 is positioned so that the opening 176 faces and is in fluid communication with the adapter 130.

In particular, on actuation of the MDI canister 190, the medication aerosol particles are discharged through the opening 176 of the actuator 174 and then are delivered through the lower section of the boot 180 and into the adapter 130.

The outlet conduit member 140 that is associated with the first chamber 110 preferably has at least one valve assembly for controlling the fluid flow into and out of the first chamber 110 as the patient inhales and exhales. In the illustrated embodiment, the outlet conduit member 140 has two valve assemblies, namely, a first valve assembly 200 and a second valve assembly 210, that are located between the ends 142, 144. The first valve assembly 200 can be thought of as an inhalation valve assembly and a second valve assembly 210 can be thought of as an exhalation valve assembly. The inhalation valve assembly 200 can be a flap valve assembly that includes a circular flap valve seat 202 that has a circular opening 204 and a complementary flap valve 206 that seats against the seat 202 to close opening 204 when the valve assembly 200 is closed. Similarly, the exhalation valve assembly 210 can be a flap valve assembly that includes a circular flap valve seat 212 that has a circular opening 214 and a complementary flap valve 216 that seats against the seat 212 to close the opening 214 when the valve assembly 210 is closed.

On inhalation, the inhalation flap valve 206 moves away from the valve seat 202 so that the aerosol particles can move from the first chamber 110 to the patient (e.g., mouth and lungs of the patient) through the opening 204 in the seat 202 and then ultimately through the outlet end 144 of the outlet conduit member 140. Conversely, on exhalation, the flap valve 206 moves toward the valve seat 202 and closes the opening 204 to prevent any flow of gas exhaled by the patient from entering into the first chamber 110, thereby avoiding re-breathing of carbon dioxide on the next inhalation. The flap valve seat 202 prevents any protrusion of the flap valve 206 through the opening 204.

The flap valve 216 of the exhalation flap valve assembly 210 presses against the flap valve seat 212 on inhalation and completely occludes the opening 214 to prevent any room air entrainment (i.e., not allowing the air from the atmosphere to enter into the outlet conduit member 140 on inhalation). On exhalation, the flap valve 216 moves away from the flap valve seat 212 for the air exhaled by the patient to escape into the atmosphere from the outlet conduit member 140 through the opening 214.

Optionally, the outlet conduit member 140 can serve as a nebulizer chamber to support the use of a nebulizer, generally shown at 300. The outlet conduit chamber 140 has a fluid inlet connector 280 formed as a part thereof for connection with a standard small volume nebulizer 300. As is known, a nebulizer is a device that changes liquid medicine into fine droplets (in aerosol or mist form) that are inhaled through some type of device, such as a mouthpiece or mask, etc. The connector 280 has one end 282 that is in fluid communication with an interior of the outlet conduit member 140 and at an opposite end 284, an opening or port is open for connection to the nebulizer 300. In the illustrated embodiment, the fluid inlet connector 280 is formed at a location between the inhalation valve assembly 200 and the outlet end 114 of the first chamber 110 for delivery of the aerosolized medication. If the valve assembly 200 is closed as when the patient exhales, the aerosolized medication is delivered into the first chamber 110 for storage thereof until the valve assembly 200 open as when the patient inhales.

It will also be understood that one or both of the first and second chambers 110, 120 can be a non-collapsible structure and instead have a fixed volume. In contrast, one or both of the first and second chambers 110, 120 can be collapsible and have a variable volume. Thus, while FIG. 1 shows the first chamber 110 as having a collapsible, variable volume structure, the opposite can equally be true.

FIGS. 2-6 show the adapter 130 according to a first embodiment of the present invention for mating and securely coupling to the inhaler (MDI) 170. The adapter 130 is a generally hollow member that extends outwardly from the second chamber 120 and is in fluid communication with an interior of the second chamber 120. In the illustrated embodiment, the adapter 130 extends outwardly from the inlet end 122 of the second chamber 120. The adapter 130 is defined by a side wall 132 that can be attached to or integrally formed with the wall of the second chamber 120 and defines the tubular structure of the adapter 130. The cross-sectional shape of the adapter 130 can be any number of different shapes with one shape being a circular cross-sectional shape as shown in the Figures. However, the adapter 130 can have a square shape or oval shape or some other shape.

The side wall 132 of the adapter 130 is thus attached to the inlet end 122 at a first end 134 thereof and the opposite end 136 thereof defines an opening into the interior of the adapter 130 which leads into an interior of the second chamber 120. As shown in FIG. 4, the cross-sectional view of the side wall 132 includes spaced apart vertical walls, with an inlet or opening being formed therebetween that forms an entrance into the interior of the second chamber 120.

The adapter 130 has a seal element 138 formed as a part thereof for providing an improved fit and seal with the inhaler 170 and more particularly, the seal element 138 is in the form of a compressible member (formed of a compressible material) that is formed on one or more surfaces of the side wall 132. In particular, the compressible seal member 138 is formed at locations where the boot 180 mates with the adapter 130 so as to provide an improve fit and seal between the boot 180 and the adapter 130. The compressible seal member 138 is thus provided at least on an inner surface 133 of the side wall 132 when the boot 180 mates with the adapter 130 by being received into the interior of the adapter 130 (i.e., received between the side wall 132). In the illustrated embodiment, the compressible seal member 138 is formed on both the inner surface 133 and an outer surface 135 of the side wall 132 and extends across the distal end (inlet end) of the side wall 132 so as to cover this distal end and provide a continuous structure from the inner surface 133 across to the outer surface 135.

As shown in FIGS. 2-6, the seal member 138 preferably extends close to the inner end (proximal end) of the side wall 132 (the interface between the side wall 132 and wall of the second chamber 120) or the seal member 138 on the inner surface 133 can contact the end 122 of the second chamber 120.

The thickness of the seal member 138 can vary depending upon a number of factors, including the size (e.g., diameter) of the boot 180 of the inhaler 170 that is received within the interior of the adapter 130 and the type of material that is used to form the seal member 138. In its non-compressed state, the diameter between the inner surface of the seal member 138 is greater than a diameter of the portion of the boot 180 that is received within the adapter 130 for mating therewith so as to form a frictional, sealed interface or fit between the boot 180 and the adapter 130.

In the illustrated embodiment, the thickness of the seal member 138 that extends along the inner surface 133 is greater than the thickness of the seal member 138 that extends along the outer surface 135; however, this does not have to be the case and the two thicknesses can be substantially the same or the thickness of the outer section can be greater. However, more material of the seal member 138 is typically provided in the interior of the adapter 130 where a coupling with the boot 180 is formed.

The material that is used to form the seal member 138 can be in the form of a highly compressible rubber material; however, other types of compressible materials can be formed. In other words, the seal member 138 is formed of a compressible rubber or foam material or similar type of material that can compress under pressure (force) but then has memory to return to its original shape after the pressure (force) is removed is suitable for use as the compressible seal member 138. As shown in FIG. 4, when the boot 180 is inserted into the adapter 130, the boot 180 compresses the seal member 138 so as to result in a secure frictional fit between the boot 180 and the adapter 130. By creating a seal at the interface between the boot 180 and the seal member 138, the aerosolized medication is discharged from the inhaler 170 into the interior of the second chamber 120 without any leaks of the medication.

As shown in FIG. 12, a cap 230 can be provided for selectively sealing the open end of the seal member 138 and for providing a venting means. The cap 230 includes a body 232 that is constructed to be sealingly coupled to the body 232 and in particular, the cap 230 is constructed to sealingly engage the seal member 138 that is disposed on the adapter 130 so as to fluidly close off the adapter 130. As will be described below, the cap 230 is designed to be placed on the adapter 130 when the inhaler 170 is not in use. The body 232 has a top wall 234 and a peripheral side wall or edge 236 that extends around the body 232 and is intended to engage the side wall of the adapter 130. The side wall 236 is formed at a right angle to the top wall 234, with an inner diameter between the side wall 236 being greater than an outer diameter of the side wall of the adapter 130 and being slightly greater or approximately equal to the outer diameter of the seal member 138 since the resiliency of the mater of the seal member 138 permits the cap 230 to be inserted on and over the seal member 138 that is disposed over the adapter 130. When the cap 230 is placed over the seal member 138, the seal member 138 will locally compress and permit a frictional fit to result between the cap 230 and the adapter 130. The frictional fit between the cap 230 and the seal member 138 permits the cap 230 to remain in place over the adapter 130 during normal use of the device.

According to one aspect of the present invention, the cap 230 has a valve feature in that the cap 230 has one or more vent opening 240 formed therethrough to permit air to selectively pass through the cap 230. In the illustrated embodiment, the cap 230 has a plurality of openings 240 formed in the central section of the cap 230 and in particular, the vent openings 240 are formed in a circular manner around a center of the cap 230. In the illustrated embodiment, there are four vent openings 240 that are spaced about 90 degrees from one another. However, it is not necessary for the vent openings 240 to be equidistant from one another and in instead, the vent openings 240 can be formed according to different patterns within the top wall. The size and shape of the individual vent openings 240 can also be varied depending upon the particular application and depending upon the level of venting that is desired.

In yet another aspect, the vent openings 240 are not always open to atmosphere but instead, a valve member or element 242 is provided and is operatively coupled to the cap 230 in the location of where the vent openings 240 are formed so that if the valve member 242 is in the open position, air can travel through the vent openings, while if the valve member 242 is in the closed position, air is not permitted to travel through the vent openings 240. In the illustrated embodiment, the valve member 242 is disposed on and coupled to an underside of the top wall 234 of the cap 230 such that the valve member 242 overlays the vent openings 240. The valve member 242 is configured such that when the patient inhales, the valve member 242 opens and air is permitted to flow within and through the vent openings 240. In contrast, when the patient exhales, the valve member 242 closes and air is prevented from flowing within and through the vent openings.

The valve member 242 can be constructed in any number of different ways so long as it performs the above function and in one embodiment, the valve member 242 is in the form of a flapper type valve as described above. It will be appreciated that in one embodiment, the valve member 242 is a single valve member that covers all of the vent openings 240 and as so soon as the patient inhales and produces a negative pressure (suction) within the second chamber 120, the valve member 242 will open by lifting away from the underside around the vent openings 240 so as to create a flow path through the vent openings 240. The valve member 242 can be attached to the underside of the cap 230 by any number of different means, including, attaching the valve member 242 at a central location to the underside, such as at a center section of the cap 230, with the vent openings 240 being formed radially around the point where the valve member 242 is attached to the underside of the cap member 230.

In one exemplary embodiment, the valve member 242 is made of a flexible resilient material that moves against the underside of the cap 230 so as to close off the vent openings 240 when positive pressure is applied thereto as when the patient exhales and conversely, when the patient inhales, the valve member 242 is drawn away from the underside of the cap 230 so as to open the vent openings 240. For example, the valve member 242 can be in the form of a sheet of material having a predetermined shape, such as circular, that covers the vent openings 240 when the valve member 242 is drawn against the underside of the cap 230.

In the embodiment where there are a plurality of valve members 242, they are arranged such that each vent opening 240 has an associated valve member 242, with each valve member 242 operating in the same manner in that application of negative pressure causes each valve member 242 to lift away from the underside of the cap 230 to open a flow path for air and application of positive pressure causes each valve member 242 to seat against the underside so as to close off each vent opening 240.

Figure 4:
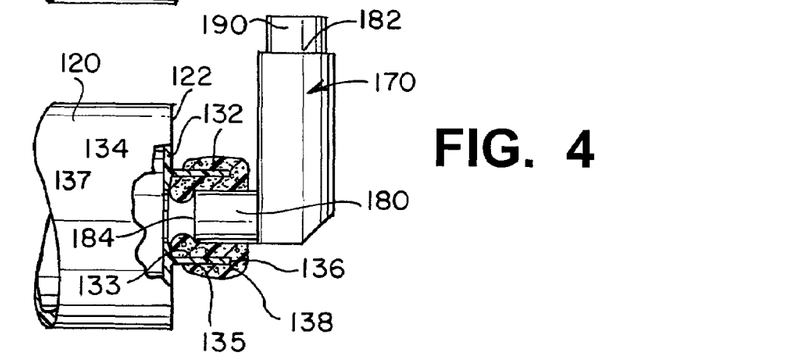
FIG. 4 is an enlarged side elevation view, in partial cross-section, of the adapter of FIG. 2 with the medication delivery device shown mated therewith.

As shown in FIG. 4, the side wall 132 does not have to be axially aligned with the edge of the opening formed through the adapter 130 and therefore an annular shoulder 137 is formed between the side wall 132 and the floor portion of the wall to which the side wall 132 is attached. This floor serves as a locator and serves to contain the seal member 138 which rests thereon.

According to the above embodiment of the present invention, the system 100 provides a closed nebulizer arrangement that offers improved performance compared to the prior art nebulizer systems which were not closed, as previously mentioned, but instead were vented to atmosphere at a location just prior to or at the interface where the nebulized medication was delivered to the patient's mask or the like. The atmospheric venting of the prior art designs leads to the dilution of the concentration of the medication being delivered to the patient, which is not desirable, since the physician initially prescribes a concentration of medication that is to be delivered to the patient and preferably, this concentration is to remain unchanged as it is delivered from the nebulizer into the patient's body. As can be seen from FIG. 1 and the accompanying description, the present system 100 does not contain an atmospheric vent that is open during the delivery of the nebulized medication. While there is a pair of valve mechanisms in the fourth conduit member 160 that is associated with the first chamber 110, these valves function so that the nebulized medication that is held within the first and second compartments 110, 120 is delivered to the patient's body as the patient inhales. As previously mentioned, on inhalation, the inhalation flap valve 206 moves away from the valve seat 202 so that the aerosol particles can move from the first chamber 110 to the patient (e.g., mouth and lungs of the patient) through the opening 204 in the seat 302 and then ultimately through the outlet end 134 of the fourth conduit member 130. The flap valve 216 of the exhalation flap valve assembly 210 presses against the flap valve seat 212 on inhalation and completely occludes the opening 214 to prevent any room air entrainment (i.e., not allowing the air from the atmosphere to enter into the fourth conduit member 130 on inhalation). This therefore leads to be a completely closed nebulizer system that ensures delivery of medication having a fixed concentration, unlike the prior art systems.

To alter the holding capacity of the first chamber 110, the distance between two adjacent ridges 166, rings of associated coils, or valleys 168 is reduced by pulling the two adjacent structures together in the case of when the structure forming the first chamber 110 has a bellows type construction.

FIGS. 8-11 show an adapter 400 according to a second embodiment of the present invention for mating and securely coupling to the inhaler (MDI) 170. The adapter 400 is a generally hollow member that extends outwardly from the second chamber 120 and is in fluid communication with an interior of the second chamber 120. In the illustrated embodiment, the adapter 400 extends outwardly from the inlet end 122 of the second chamber 120. The adapter 400 is defined by a side wall 402 that can be attached to or integrally formed with the wall of the second chamber 120 and defines the tubular structure of the adapter 130. The cross-sectional shape of the adapter 400 can be any number of different shapes with one shape being a circular cross-sectional shape as shown in the Figures. However, the adapter 400 can have a square shape or oval shape or some other shape so long as the inhaler 170 can mate therewith.

Figures 9, 9A, 10:
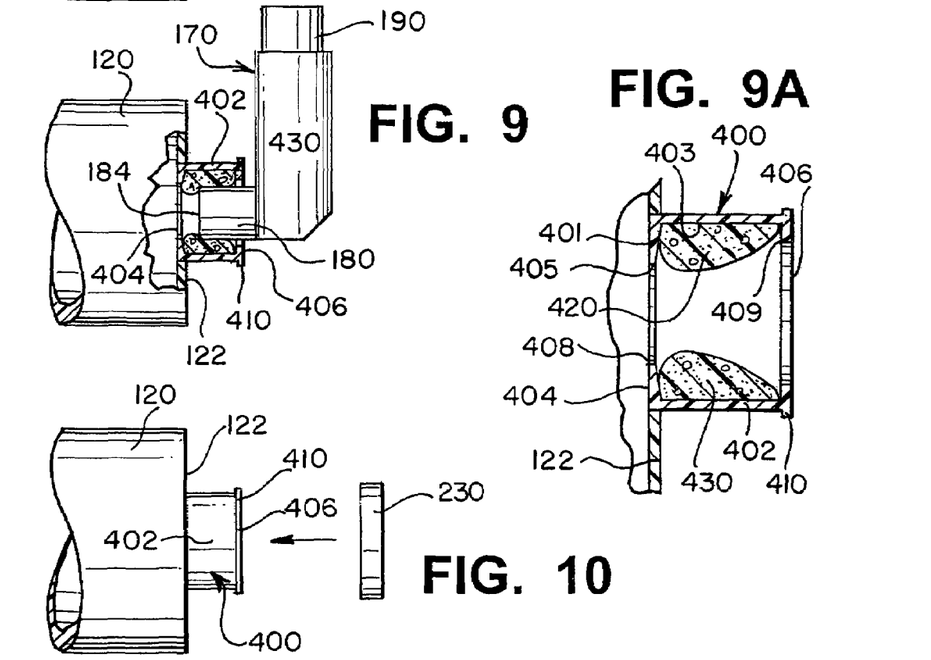
FIG. 9 is an enlarged side elevation view, in partial cross-section, of the adapter of FIG. 8 with the medication delivery device shown mated therewith.
FIG. 9A is an enlarged cross-sectional view of the adapter of FIG. 8.
FIG. 10 is an enlarged side elevation view of the adapter of FIG. 8 with a cap for insertion in the adapter being shown exploded therefrom.
Figure 11:
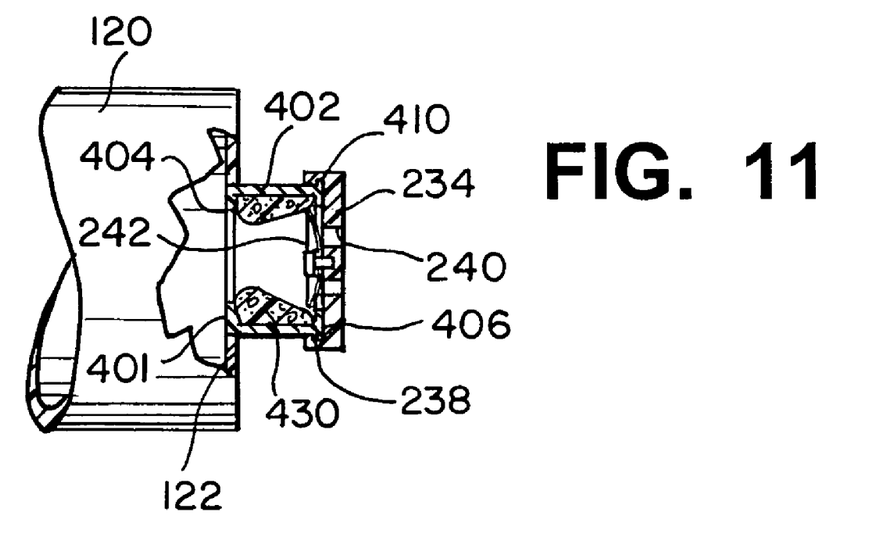
FIG. 11 is a side elevation view, in partial cross-section, of the adapter of FIG. 8 with the cap mated therewith and in cross-section.

The side wall 402 of the adapter 400 is thus attached to the inlet end 122 at a first end 404 thereof and the opposite end 406 thereof defines an opening into the interior of the adapter 400 which leads into an interior of the second chamber 120. As shown in FIG. 9A, the cross-sectional view of the side wall 402 includes spaced apart vertical walls, with an inlet or opening being formed therebetween that forms an entrance into the interior of the second chamber 120.

It will be appreciated that the adapter 400 can be formed so as to plug and mate with the opening formed at the inlet end 122 instead of being integrally formed with the end 122 of the second chamber 120 and in this embodiment, the adapter 400 includes an annular disk shaped portion 401 that is received within the opening formed at the inlet end 122. The side wall 402 is integrally formed with and extends outwardly from the disk shaped portion 401. For example, the side wall 402 can be formed at a right angle to the disk shaped portion 401, with an opening (bore) that is defined by the side wall 402 extending through an opening 408 formed in the disk shaped portion 401 and providing communication with the second chamber 120.

An upper edge (end 406) of the side wall 402 includes an inwardly directed annular lip 409 as well as an outwardly directed lip 410. As shown in FIG. 9A, the edge 405 of the disk-shaped portion 401 that defines the opening 408 is not necessarily axially aligned with the side wall 402 but as illustrated, the side wall 402 is located radially outward from the edge 405 so as to form an annular shoulder therebetween. As shown, the inner edge of the lip 409 and the edge 405 are not within the same plane but instead, the inner edge of the lip 409 does not extend all the way to the edge 405. It will therefore be appreciated that there is a space 420 formed and defined between the underside of the lip 409 (which acts as a ceiling) and the portion of the disk 401 that extends from the side wall 402 to the edge 405 (which acts as a floor).

As with the prior embodiment, the adapter 400 includes a seal element 430 formed as a part thereof for providing an improved fit and seal with the inhaler 170 and more particularly, the seal element 430 is in the form of a compressible member (formed of a compressible material) that is formed on one or more surfaces of the side wall 402. In particular, the compressible seal member 430 is formed at locations where the boot 180 mates with the adapter 400 so as to provide an improve fit and seal between the boot 180 and the adapter 400. The compressible seal member 430 is thus provided on an inner surface 403 of the side wall 402 when the boot 180 mates with the adapter 130 by being received into the interior of the adapter 400 (i.e., received between the side wall 402). In the illustrated embodiment, the compressible seal member 430 is provided in the space 420 and in particular, along the inner surface 403 between the underside of the lip 409 and the portion of the disk 401 that extends from the side wall 402 to the edge 405. The lip 409 and this floor portion of the disk 401 serves to locate and contain the compressible seal member 430.

The thickness of the seal member 430 can vary depending upon a number of factors, including the size (e.g., diameter) of the boot 180 of the inhaler 170 that is received within the interior of the adapter 130 and the type of material that is used to form the seal member 430. In its non-compressed state, the diameter between the inner surface of the seal member 430 is greater than a diameter of the portion of the boot 180 that is received within the adapter 400 for mating therewith so as to form a frictional, sealed interface or fit between the boot 180 and the adapter 400.

FIG. 9 shows the boot 180 received in the adapter 400 and compressing the seal member 430 so as to provide the desired sealing action between the inhaler 170 and the adapter 400.

Figure 12:
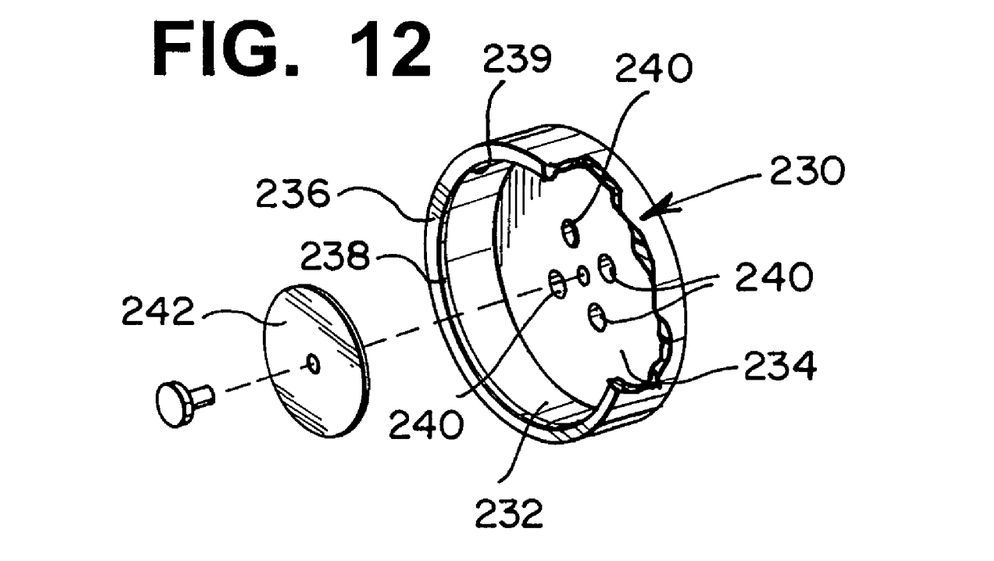
FIG. 12 is an exploded view, in partial cross-section, of a valve member of the cap.

In yet another aspect, a locking feature can be provided for locking or securing the cap 230 to the respective adapter. For example, the cap 230, as shown in FIG. 12, can have a bottom lip 239 that extends radially inwardly as to form an inner shoulder with the side wall 232. The bottom lip 230 is intended to mate with, e.g., snap-fittingly, with the outwardly extending lip 410 that is shown in FIG. 9A as part of the adapter 400. When the cap 230 is received over the adapter 400, the lip 239 is received underneath the lip 410 for securing the cap 230 on the adapter 400.

As shown in FIGS. 5-12, instead of having a cap 230, the adapter 130 includes a vent feature in the form of a plug 540 instead of the cap 230. The plug 540 is a substantially hollow member that includes a first end 542 that is a substantially closed end and an opposing second end 544 that is substantially open and is designed to be received between the side wall 502 of the adapter 130. The plug 540 therefore generally has the same shape as the adapter 130 to permit mating of the plug 540 and the adapter 130. In order to create a frictional fit with the adapter 130, the plug 540 has a tapered construction to permit reception of the plug 540 between the side wall 132. In other words, the diameter of the plug 540 from first end 542 to second end 544 varies, with the second end 544 having a smaller diameter.

Figure 5:
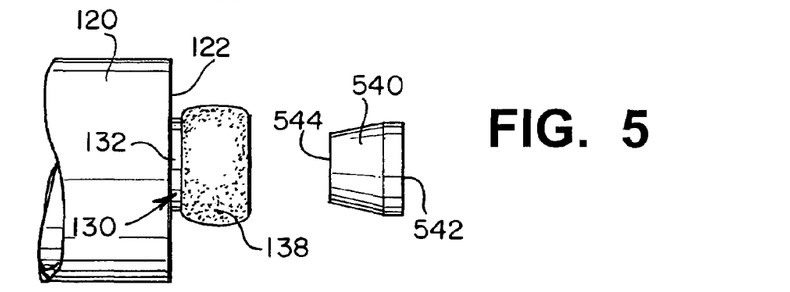
FIG. 5 is an enlarged side elevation view of the adapter of FIG. 2 with a plug for insertion in the adapter being shown exploded therefrom.
Figure 6:
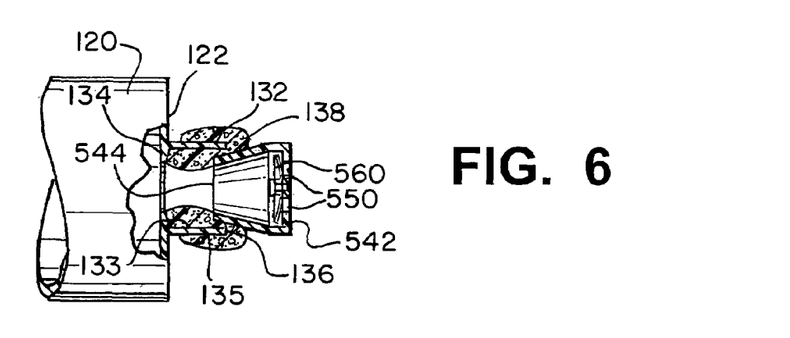
FIG. 6 is a side elevation view, in partial cross-section, of the adapter of FIG. 2 with the plug mated therewith and in cross-section.

Like the cap 230, the plug 540 is designed to be placed on the adapter 500 when the inhaler 170 is not in use. The outer diameter of the second end 544 of the plug 540 is greater than an inner diameter of the side wall of the adapter 130 and is slightly greater or approximately equal to the outer diameter of the seal member 530 since the resiliency of the mater of the seal member 530 permits the plug 540 to be inserted and to compress the seal member 530 that is disposed over the adapter 130. When the plug 540 is inserted between the side wall 132 of the adapter 130, the seal member 530 will locally compress and permit a frictional fit to result between the plug 540 and the adapter 130. The frictional fit between the plug 540 and the seal member 530 permits the plug 540 to remain in place over the adapter 130 during normal use of the device.

According to one aspect of the present invention, the plug 540 has a valve feature in that the plug 540 has one or more vent opening 550 formed therethrough to permit air to selectively pass through the plug 540. In the illustrated embodiment, the plug 540 has a plurality of openings 550 formed in the central section of the plug 540 and in particular, the vent openings 550 are formed in a circular manner around a center of the plug 540. In the illustrated embodiment, there are four vent openings 550 that are spaced about 90 degrees from one another. However, it is not necessary for the vent openings 550 to be equidistant from one another and in instead, the vent openings 550 can be formed according to different patterns within the top wall. The size and shape of the individual vent openings 550 can also be varied depending upon the particular application and depending upon the level of venting that is desired.

Figure 7:
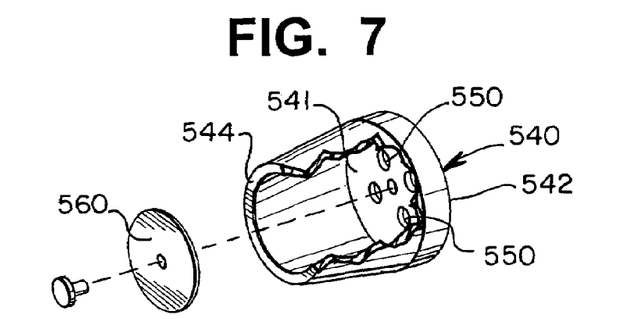
FIG. 7 is an exploded view, in partial cross-section, of a valve member of the plug.
Figure 8:
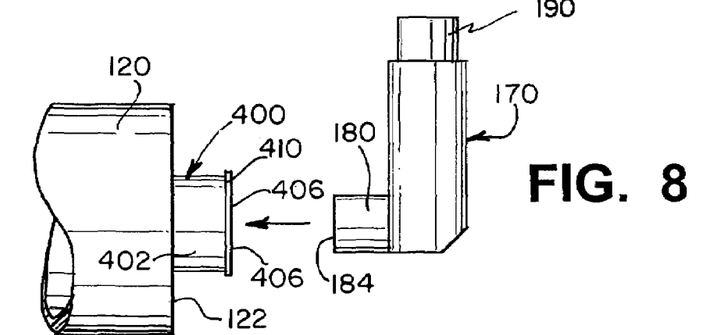
FIG. 8 is an enlarged side elevation view of an adapter according to another embodiment with a medication delivery device being exploded therefrom.

In yet another aspect, the vent openings 550 are not always open to atmosphere but instead, a valve member or element 560 is provided and is operatively coupled to the plug 540 in the location of where the vent openings 550 are formed so that if the valve member 560 is in the open position, air can travel through the vent openings, while if the valve member 560 is in the closed position, air is not permitted to travel through the vent openings 550. In the illustrated embodiment, the valve member 560 is disposed on and coupled to an underside of the top wall 541 of the plug 540 such that the valve member 560 overlays the vent openings 550. The valve member 560 is configured such that when the patient inhales, the valve member 560 opens and air is permitted to flow within and through the vent openings 550. In contrast, when the patient exhales, the valve member 560 closes and air is prevented from flowing within and through the vent openings 550.

The valve member 560 can be constructed in any number of different ways so long as it performs the above function and in one embodiment, the valve member 560 is in the form of a flapper type valve as described above. It will be appreciated that in one embodiment, the valve member 560 is a single valve member that covers all of the vent openings 550 and as so soon as the patient inhales and produces a negative pressure (suction) within the second chamber 120, the valve member 560 will open by lifting away from the underside around the vent openings 550 so as to create a flow path through the vent openings 550. The valve member 560 can be attached to the underside of the plug 540 by any number of different means, including, attaching the valve member 560 at a central location to the underside, such as at a center section of the plug 540, with the vent openings 550 being formed radially around the point where the valve member 560 is attached to the underside of the plug 540.

In one exemplary embodiment, the valve member 560 is made of a flexible resilient material that moves against the underside of the plug 540 so as to close off the vent openings 550 when positive pressure is applied thereto as when the patient exhales and conversely, when the patient inhales, the valve member 560 is drawn away from the underside of the plug 540 so as to open the vent openings 550. For example, the valve member 560 can be in the form of a sheet of material having a predetermined shape, such as circular, that covers the vent openings 550 when the valve member 560 is drawn against the underside of the plug 540.

In the embodiment where there are a plurality of valve members 560, they are arranged such that each vent opening 550 has an associated valve member 560, with each valve member 560 operating in the same manner in that application of negative pressure causes each valve member 560 to lift away from the underside of the plug 540 to open a flow path for air and application of positive pressure causes each valve member 560 to seat against the underside so as to close off each vent opening 550.

The thickness of the seal member 530 can vary depending upon a number of factors, including the size (e.g., diameter) of the boot 180 of the inhaler 170 that is received within the interior of the adapter 130 and the type of material that is used to form the seal member 530. In its non-compressed state, the diameter between the inner surface of the seal member 530 is greater than a diameter of the portion of the boot 180 that is received within the adapter 130 for mating therewith so as to form a frictional, sealed interface or fit between the boot 180 and the adapter 130.

It will be appreciated that any number of different interface members (system) can be used and that the system 100 is merely exemplary in nature and not limiting of the adapter present invention. More specifically, PCT/US2005/010274, filed Mar. 29, 2005, by the present applicant and which is hereby incorporated by reference in its entirety, discloses a number of devices and interface elements that can be used with the adapters of the present invention.

Each of the above described devices/accessories can be used in conventional inhalation equipment settings and thus can be used with either a nebulizer, an MDI, or both and they overcome the deficiencies that are associated with the prior art aerosol inhalation systems.

Having described embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An aerosol inhalation system comprising:
a first conduit member for delivering medication in the form of aerosol particles to a patient;
a first holding chamber for holding the aerosol particles prior to deliver to the first conduit member; and
a valve mechanism associated with the first conduit member and including a first valve assembly and a second valve assembly, the first valve assembly being positionable between an open position and a closed position where the fluid is prevented from flowing between the first holding chamber and the first conduit member as when the patient exhales, the first valve assembly assuming the open position as the patient inhales, the second valve assembly being positionable between an open position where the first conduit member is vented to atmosphere as when the patient exhales and a closed position when the patient inhales and the first valve assembly opens, and a first device in fluid communication with the first holding chamber for producing the aerosol particles and being sealingly yet releasably received within an adapter that forms an entrance into the first holding chamber, the adapter having a compressible material disposed thereon which is at least partially compressed by insertion of the first device to form the seal between the first device and the adapter;
wherein the aerosol inhalation apparatus is a closed system and is therefore capable of delivering a fixed concentration of the medication to the patient due to the second valve assembly being closed when the patient inhales and the medication is delivered to the patient;
wherein the adapter is a hollow structure with a side wall that defines a bore formed therethrough, the wall having an inner surface, with the compressible material being formed at least one an inner surface of the side wall of the adapter; the side wall extending outwardly from a main wall and has an inner diameter that is greater than a diameter of an opening formed in the main wall that is axially aligned with the bore so as to form a shoulder between the side wall and main wall which defines a floor for locating and supporting the compressible material, wherein an upper edge of the side wall includes an inwardly directed annular lip that defines a ceiling and overlies the floor and serves to locate and support the compressible material.

2. The system of claim 1, wherein the adapter is integrally formed with the first holding chamber and extends outwardly therefrom at a substantially right angle.

3. The system of claim 1, wherein the diameter of the opening in the main wall is less than the diameter of the side wall.

4. The system of claim 1, wherein the compressible material one of a foam material and a rubber material.

5. An aerosol inhalation system comprising:
a first conduit member for delivering medication in the form of aerosol particles to a patient;
a first holding chamber for holding the aerosol particles prior to deliver to the first conduit member;
a valve mechanism associated with the first conduit member and including a first valve assembly and a second valve assembly, the first valve assembly being positionable between an open position and a closed position where the fluid is prevented from flowing between the first holding chamber and the first conduit member as when the patient exhales, the first valve assembly assuming the open position as the patient inhales, the second valve assembly being positionable between an open position where the first conduit member is vented to atmosphere as when the patient exhales and a closed position when the patient inhales and the first valve assembly opens, and a first device in fluid communication with the first holding chamber for producing the aerosol particles and being sealingly yet releasably received within an adapter that forms an entrance into the first holding chamber, the adapter having a compressible material disposed thereon which is at least partially compressed by insertion of the first device to form the seal between the first device and the adapter; and a cap that is constructed to seal the adapter when the device is removed therefrom, the cap being frictionally fit to an open end of the adapter, the cap having a plurality of vent openings formed therethrough;

wherein the aerosol inhalation apparatus is a closed system and is therefore capable of delivering a fixed concentration of the medication to the patient due to the second valve assembly being closed when the patient inhales and the medication is delivered to the patient.

6. The system of claim 5, wherein the openings are formed equidistantly from one another.

7. The system of claim 5, further including: a valve member that is in selective communication with the vent openings such that in a closed position, the valve member prevents air to the vent openings and in an open position, the valve member permits air to flow through the vent openings into the holding chamber.

8. The system of claim 7, wherein the valve member comprises a flexible membrane that is attached to an underside of the cap in a central region between the vent openings with outer peripheral edges of the flexible membrane covering the vent openings in the closed position.

9. The system of claim 7, wherein the valve member comprises a plurality of flexible membranes that are attached to an underside of the cap, with each vent opening having an associated flexible membrane.

10. An aerosol inhalation system comprising:
a first conduit member for delivering medication in the form of aerosol particles to a patient;
a first holding chamber for holding the aerosol particles prior to deliver to the first conduit member;
a valve mechanism associated with the first conduit member and including a first valve assembty and a second valve assembly, the first valve assembly being positionable between an open position and a closed position where the fluid is prevented from flowing between the first holding chamber and the first conduit member as when the patient exhales, the first valve assembly assuming the open position as the patient inhales, the second valve assembly being positionable between an open position where the first conduit member is vented to atmosphere as when the patient exhales and a closed position when the patient inhales and the first valve assembly opens, and a first device in fluid communication with the first holding chamber for producing the aerosol particles and being sealingly yet releasably received within an adapter that forms an entrance into the first holding chamber, the adapter having a compressible material disposed thereon which is at least partially compressed by insertion of the first device to form the seal between the first device and the adapter; and a plug that is constructed to seal the adapter when the device is removed therefrom, the plug being frictionally fit to an open end of the adapter, the plug having a plurality of vent openings formed therethrough;

wherein the aerosol inhalation apparatus is a closed system and is therefore capable of delivering a fixed concentration of the medication to the patient due to the second valve assembly being closed when the patient inhales and the medication is delivered to the patient.

11. The system of claim 10, wherein the openings are formed equidistantly from one another.

12. The system of claim 10, further including: a valve member that is in selective communication with the vent openings such that in a closed position, the valve member prevents air to the vent openings and in an open position, the valve member permits air to flow through the vent openings into the holding chamber.

13. The system of claim 12, wherein the valve member comprises a flexible membrane that is attached to an underside of the plug in a central region between the vent openings with outer peripheral edges of the flexible membrane covering the vent openings in the closed position.

14. The system of claim 12, wherein the valve member comprises a plurality of flexible membranes that are attached to an underside of the cap, with each vent opening having an associated flexible membrane.

15. The system of claim 1, wherein the first conduit member comprises a hollow conduit body that carries the aerosol particles from the first holding chamber when the patient inhales for purpose of delivering the medication into the patient and carries discharged gases from the patient when the patient exhales for purpose of venting these gases to atmosphere.

16. The system of claim 1, wherein the first holding chamber has a variable interior volume.

17. The system of claim 16, wherein the first holding chamber is defined by a body that is collapsible and expandable in length so as to vary the interior volume.

18. The system of claim 1, wherein the first valve assembly is disposed proximate an interface between the first conduit member and the first holding chamber and includes a first valve and a first valve seat having an opening extending therebrough for permitting selective flow of the aerosol particles when the first valve is open relative to the first valve seat, the first valve sealingly seating against the first valve seat in the closed position.

19. The system of claim 1, wherein the second valve assembly is disposed between the first valve assembly and an open outlet end of the first conduit member, the second valve assembly including a second valve and a second valve seat having an opening extending therethrough for permitting the discharged gases to flow into atmosphere when the second valve is open relative to the second valve seat, the second valve sealingly seating against the second valve seat in the closed position.

20. The system according to claim 1, wherein the device comprises a metered dose inhaler.

21. An aerosol inhalation system comprising:
a first conduit member for delivering medication in the form of aerosol particles to a patient;
a first holding chamber for holding the aerosol particles prior to deliver to the first conduit member;

a valve mechanism associated with the first conduit member and including a first valve assembly and a second valve assembly, the first valve assembly being positionable between an open position and a closed position where the fluid is prevented from flowing between the first holding chamber and the first conduit member as when the patient exhales, the first valve assembly assuming the open position as the patient inhales, the second valve assembly being positionable between an open position where the first conduit member is vented to atmosphere as when the patient exhales and a closed position when the patient inhales and the first valve assembly opens, and a first device in fluid communication with the first holding chamber for producing the aerosol particles and being sealingly yet releasably received within an adapter that forms an entrance into the first holding chamber, the adapter having a compressible material disposed thereon which is at least partially compressed by insertion of the first device to form the seal between the first device and the adapter; and a second holding chamber in fluid communication with the first holding chamber and including the adapter for attachment to the device;

wherein the aerosol inhalation apparatus is a closed system and is therefore capable of delivering a fixed concentration of the medication to the patient due to the second valve assembly being closed when the patient inhales and the medication is delivered to the patient.

22. The system according to claim 1, wherein the first conduit includes a second port for attachment to a second device.

23. The system of claim 1, wherein the second device comprises a nebulizer.

* * * * *